United States Patent
Jacobson et al.

(10) Patent No.: US 8,790,626 B2
(45) Date of Patent: *Jul. 29, 2014

(54) METHOD FOR TREATING HAIR GROWTH DISORDERS, SUCH AS FEMALE PATTERN ALOPECIA, AND COMPOSITIONS USEFUL THEREFORE

(75) Inventors: Elaine L. Jacobson, Tucson, AZ (US); Myron K. Jacobson, Tucson, AZ (US); Hyuntae Kim, Tucson, AZ (US); Donna L. Coyle, Tucson, AZ (US); William R. Coyle, Tucson, AZ (US)

(73) Assignees: The University of Kentucky, Lexington, KY (US); The Arizona Board of Regents on Behalf of the University of Arizona, Tucson, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/305,079

(22) Filed: Nov. 28, 2011

(65) Prior Publication Data

US 2012/0093739 A1 Apr. 19, 2012

Related U.S. Application Data

(63) Continuation of application No. 11/922,378, filed as application No. PCT/US2006/024921 on Jun. 26, 2006, now Pat. No. 8,114,390.

(60) Provisional application No. 60/693,716, filed on Jun. 24, 2005.

(51) Int. Cl.
*A61Q 5/02* (2006.01)
*A61Q 5/00* (2006.01)

(52) U.S. Cl.
USPC ............................. 424/70.1; 424/47; 514/356

(58) Field of Classification Search
None
See application file for complete search history.

(56) References Cited

U.S. PATENT DOCUMENTS

| | | | | |
|---|---|---|---|---|
| 5,157,036 A | * | 10/1992 | Grollier | 514/256 |
| 8,114,390 B2 | * | 2/2012 | Jacobson et al. | 424/70.1 |
| 2004/0081672 A1 | * | 4/2004 | Gupta | 424/401 |
| 2004/0198776 A1 | * | 10/2004 | Jaccobson et al. | 514/355 |
| 2005/0019356 A1 | * | 1/2005 | Bissett et al. | 424/401 |
| 2005/0180940 A1 | * | 8/2005 | Puma | 424/70.24 |

* cited by examiner

*Primary Examiner* — Jyothsna Venkat
(74) *Attorney, Agent, or Firm* — Abelman, Frayne & Schwab

(57) ABSTRACT

The invention relates to formulations useful in treating hair disorders, improving the health of hair, increasing hair growth, and in increasing the niacin content of hair follicles. Nicotinic acid alkyl esters having a straight chain alkyl group of from 1 to 22 methylene units, preferably from 6 to 16 methylene units, and most preferably from 8 to 14 methyl units, may be used, alone or in combinations for treating these conditions.

4 Claims, 2 Drawing Sheets

Figure Legend
Figure 1: An example of the effect of nicotinic acid derivatives on thinning hair as documented by 35 mm photography at baseline and 6 months of application.
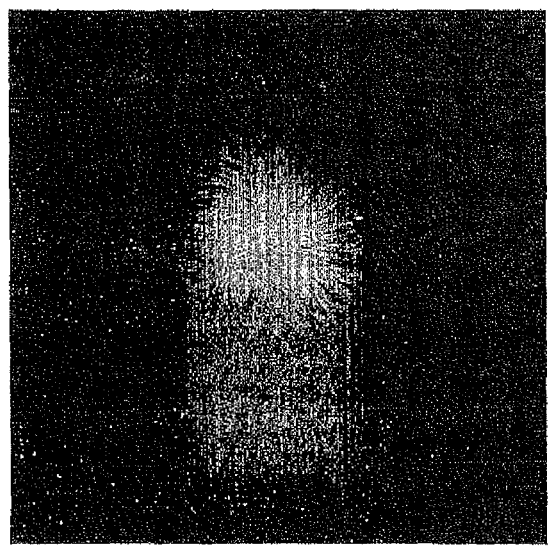
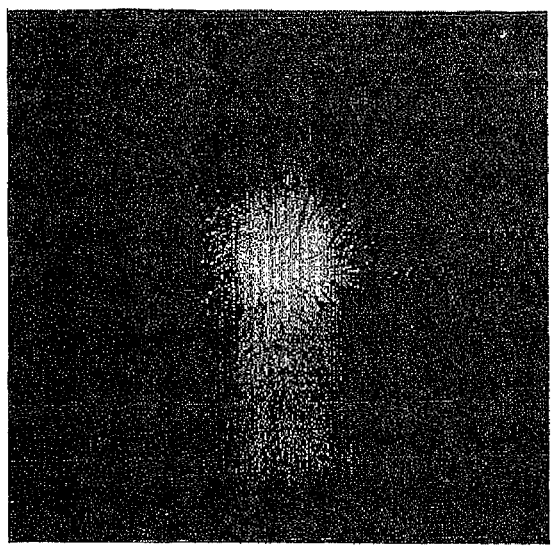
Baseline
A
6 months
B Figure: Effect of lipophilic derivatives of niacin on hair follicle NAD

METHOD FOR TREATING HAIR GROWTH DISORDERS, SUCH AS FEMALE PATTERN ALOPECIA, AND COMPOSITIONS USEFUL THEREFORE

RELATED APPLICATION

This application is a continuation of application Ser. No. 11/922,378, filed Dec. 13, 2007 now U.S. Pat. No. 8,114,390, which is a §371 application of PCT/US2006/24921, filed Jun. 26, 2006, which claims priority of Ser. No. 60/693,716, filed Jun. 24, 2005, incorporated by reference.

FIELD OF THE INVENTION

This invention relates to methods for treating disorders such as hair loss, pattern hair loss (alopecia), in particular. It also relates to increasing the content of NAD in hair follicles, thus increasing the energy available in these tissues, which in turn leads to enhanced growth, fullness, thickness, and overall quality of scalp hair. Even more particularly, the invention relates to treatment of these conditions in females.

BACKGROUND AND PRIOR ART

Female pattern hair loss (alopecia) affects approximately 20 million women. Hair loss begins at puberty and progresses throughout life. Early detection of the condition is difficult, which is unfortunate, since early diagnosis and treatment are important in achieving optimal therapy. While the pattern of hair loss varies considerably, a decreased hair count over the entire top of the scalp commonly occurs. A good indicator of female pattern hair loss is a widening part line or a thinning ponytail. Typically, daily hair loss counts do not exceed 100-125 hairs; however hair follicles that enter the telogen phase do not reenter the anagen growth phase, resulting in a slow net loss of active follicles. The treatment options for this condition are limited and include hair transplants, hormonal supplementation and minoxidil, a drug that affects calcium homeostasis. See, Li, et al., *J Invest Dermatol*, 117(6):1594-1600 (2001). Topical 2% and minoxidil, the only approved drug therapies for this condition.

The limited treatment options available for female alopecia has led to the search for other agents that can provide benefit for this condition. A potential candidate for hair growth promotion is niacin (nicotinic acid). Studies have identified several possible mechanisms suggesting that nicotinic acid may benefit these conditions. The major bioactive form of niacin, nicotinamide adenine dinucleotide (NAD) plays a central role in cellular energy metabolism and, the hair follicle has high energy requirements (Jacobson, et al., *J Photochem Photobiol B* 63(1-3):141-7 (2001)). NAD is also the substrate for enzymes involved in the maintenance of genomic integrity Jacobson, et al., *Trends Biochem Sci*, 24(11):415-417 (1999)) and calcium homeostasis (Lee, *Curr. Mol. Med.,* 4(3):227-237 (2004)). Additionally, skin has been shown to contain niacin receptors that stimulate leptin release (Kim, et al., *J. Invest. Dermatol.,* 9:347 (2002)) and downstream regulators in the leptin pathway are involved in skin homeostasis (Komuves, et al., *J Invest Dermatol*, 115(3):361-367 (2000)) and hair follicle cycling (Sano, et al., *EMBO J.,* 18(17):4657-4668 (1999)). While either niacin or its other vitamin form, niacinamide, have the potential to be converted to NAD, the nicotinic acid receptor responds only to niacin (Tunaru, et al., *Nat. Med.,* 9(3):352-355 (2003)).

While niacin has the potential to provide benefit to skin and scalp, delivery of niacin per se is not feasible in appreciable amounts, as it causes intense vasodilation at the site of application and its physical properties do not allow it to achieve a prolonged residence time in the skin. This has led to the development of myristyl nicotinate, a niacin derivative that effects delivery to skin cells without vasodilation and creates a residence time allowing conversion to NAD (Jacobson, et al., *J. Invest. Dermatol.,* 114:849 (2000), and U.S. Pat. No. 6,337,065, both of which are incorporated by reference) and stimulation of the nicotinic acid receptor. (Tunaru, et al., supra). Myristyl nicotinate has been shown to promote epidermal differentiation leading to strong enhancement of skin barrier integrity (Jacobson, et al., in Alberts, et al., ed. Fundamentals of Cancer Prevention (Springer, 2005, pgs. 139-160). Another niacin derivative, octyl nicotinate, stimulates blood flow and oxygen delivery to tissue. See, e.g., U.S. Pat. No. 6,924,299, incorporated by reference in its entirety. The '299 patent, however, is silent as to the use of the described compounds in the context of hair growth or, treatment of disorders of hair growth, or any related conditions.

A feature of the invention thus relates to methods for treating hair growth disorders, such as female pattern, baldness, or alopecia, via the administration of one or more nicotinic acid alkyl esters. In some cases, administration of one of these compounds will be sufficient, whereas in other scenarios, mixtures of two or more in a composition or formulation, will be desired.

When two or more of these nicotinic acid alkyl esters are used in composition form, such compositions are also a feature of this invention.

Further features of the invention and its operation will be clear from the discussion which follows.

SUMMARY OF THE INVENTION

The invention relates to compositions which are useful in the stimulation of hair follicles, with a resulting benefit of treating hair growth disorders, such as alopecia, in females in particular. Methods of treatment of relevant populations are also a feature of the invention.

The compositions, in their broadest aspect, comprise at least two nicotinic acid alkyl esters. The first of these is a nicotinic acid alkyl ester which delivers niacin to cells, hair follicle cells in particular, without vasodilation, wherein the nicotinic acid alkyl ester has sufficient residence time to be converted to niacin without the adverse effect of vasodilation.

The second nicotinic acid alkyl ester is one which stimulates blood flow, and hence oxygen delivery to the cells.

The first nicotinic acid alkyl ester is preferably one where the alkyl moiety comprises at least 11 carbon residues, and up to 22 carbon residues, i.e., C11, C12, C13, C14, C15, C16, C17, C18, C19, C20, C21 and C22 alkyl esters. The second nicotinic acid alkyl ester is one where the alkyl group is shorter than that in the first compound, and is preferably a C6, C7, C8, C9, or C10 alkyl ester.

More preferably, the compositions contain a first nicotinic acid alkyl ester where the alkyl moiety contains from 11 to 16 carbon atoms, and the second one from 8 to 10 carbon atoms. Most preferably, the composition comprises a C14 nicotinic acid alkylester, and a C8 nicotinic acid alkyl ester. Optionally, ingredients such as those set forth in U.S. Pat. No. 6,337,065, U.S. Pat. No. 6,464,942, and/or U.S. Pat. No. 6,924,299, all of which are incorporated by reference, may be included in the composition.

Either of the first and second nicotinic acid alkyl esters, as described supra, may be used alone, or they may be combined in a composition as described supra. When used alone, any nicotinic acid alkyl ester with an alkyl moiety of from about 8 carbons to about 16 carbons, may be used, with the C8 and/or C14 nicotinic acid alkyl esters being especially preferred. When used as a combination, e.g., a composition of two or more nicotinic acid alkyl esters, the preferred formulations are as described, supra.

BRIEF DESCRIPTION OF THE FIGURES

FIGS. 1A and 1B are "before and after" photos which show the impact of the formulations of the invention on hair growth.

DETAILED DESCRIPTION OF PREFERRED EMBODIMENTS

Example 1

Figure 2:
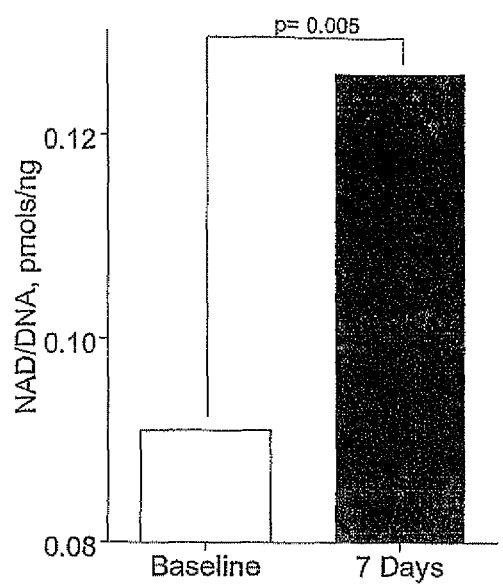
FIG. 2 shows the data of Table 2, in graphic form.

Sixty female subjects, ages 20-80, who completed an informed consent procedure with Ludwig type I-III female pattern hair loss (Ludwig, et al., *Br. J. Dermatol.*, 97(3):247-254 (1977)) were enrolled in a 6-month pilot study using a double blinded, placebo controlled design. Subjects were assigned randomly to the placebo (20, vehicle only) or active groups (40, vehicle containing 0.5% octyl nicotinate and 5.0% myristryl nicotinate). Dispensed products were packaged in identical containers. Trisiloxane and dimethicone were major components of the formulation. Since the actives are vitamin-derived substances, both the placebo and the active preparations studied are classified as cosmetics under the current FDA guidelines.

At baseline, subjects were dispensed a one month supply of assigned study product. The first dose was applied at the research center by a study nurse. Subjects were instructed to apply the formula, at night, in 6 metered doses to the scalp in the following manner: one drop each to the right anterior scalp, left anterior scalp, right middle top of the head, left middle top of the head, right posterior scalp, and left posterior scalp. If the hair was washed, the study medication was applied following hair washing. All subjects were supplied with the same shampoo. The frequency of hair washing was self selected. Subjects were asked to maintain the entry style, color, and curl of their hair throughout the study.

Subjects returned at monthly intervals for evaluation of increased hair fullness, scalp irritation, or other adverse events and product dispensing. They were asked to shampoo the morning of study visit and to avoid applying styling products. Subjects were also asked to assess the appearance of their hair. Standardized photography was used for the assessment of hair fullness since increases in hair fullness over the 6-month study period are normally not detectable by either the investigator or the subjects. At baseline, month 3, and month 6, photos of the scalp vertex, with the hair combed away from the vertex like the spokes of the wheel, and the central partline, with the hair combed smoothly to both sides of the head. These images were taken in duplicate with one set provided to the subjects for personal comparison while the second set remained at the study center. Standardized 35 mm photography was conducted at baseline, 2, 4, and 6 months as follows: vertex view with hair combed away from the crown, superior view with hair parted in midline, frontal view with headband to reveal the anterior hairline. The images were taken with the subject's head in a 3-point mount specially designed for hair loss photography. Evaluation was completed on the 6 month photographs as this represents a minimal time to detect changes in hair fullness.

Of the total subjects enrolled in the study, 32 of 40 active and 12 of 20 placebo subjects completed the study. A relatively high withdrawal rate is typical for hair fullness/growth studies but it is interesting to note that proportionally twice as many subjects in the placebo group withdrew from the study. Overall tolerability of the topical formulations was very good. There were no serious adverse events reported and the mild adverse events included 9 reports of scalp stinging, 2 of scalp burning, 12 of scalp itching, 4 reports of scalp redness, and 7 reports of eye irritation. These events occurred in both placebo and active groups indicating that the volatile vehicle and not the active ingredients was the source of the irritation.

The study yielded investigator assessments, subject assessments, and photographic assessments. Statistical Polaroid photos and subject assessments revealed a positive trend, but did not reach significance at a p value of 0.05, which was not unexpected for a 6-month study. The key assessment was based on the standardized 35 mm photographs that were evaluated by a blinded investigator for assessment of improvement in hair fullness. Each set of images was rated on a scale of minus 1 for decreased hair fullness, zero for no change, or plus 1 for increased hair fullness. These data are summarized in Table 1. The data comparing the placebo and active groups demonstrate an increased benefit for the active group with a p value of 0.04 as analyzed by the one tailed Mann Whitney test for nonparametric data. The placebo effect observed in this study is not uncommon for hair fullness studies. An example of the effect of nicotinic acid derivatives on thinning hair as documented by 35 mm photography at baseline and 6 months of application is shown in FIG. 1.

TABLE 1

Evaluation of nicotinic acid derivatives on female pattern alopecia

| Group | No of subjects | Scoring of hair growth number of subjects (% of total) | | | p value[#] |
|---|---|---|---|---|---|
| | | Decrease | No change | Increase | |
| Placebo | 20* (12[‡]) | 1 (8%) | 7 (59%) | 4 (33%) | — |
| Active[¶] | 40* (32[‡]) | 2 (6%) | 8 (25%) | 22 (69%) | 0.04 |

*number of subjects enrolled in study
[‡]number of subjects who completed the study
[#]active compared to placebo for one tailed Mann Whitney test
[¶]active contained 0.5% octyl nicotinate and 5.0% myristyl nicotinate Example 2

This example describes how application of the nicotinic acid alkyl esters of the invention improved the energy status of hair follicles, by increasing NAD content therein.

Hair samples were taken from subjects treated with the formulation of Example 1, and tested for NAD content, as well as DNA content, using art recognized methods. The results follow, in Table 2, and FIG. 2.

TABLE 2

| Subject | NAD-DNA pmol/ng Baseline | NAD/DNA pmol/ng 7 Days | Change | % Change |
|---|---|---|---|---|
| 1 | 0.136 | 0.194 | 0.058 | 43 |
| 2 | 0.104 | 0.157 | 0.053 | 51 |
| 3 | 0.080 | 0.137 | 0.057 | 71 |
| 4 | 0.107 | 0.132 | 0.025 | 23 |
| 5 | 0.062 | 0.085 | 0.023 | 37 |
| 6 | 0.069 | 0.072 | 0.004 | 51 |
| 7 | 0.079 | 0.103 | 0.025 | 31 |

TABLE 2-continued

| Subject | NAD-DNA pmol/ng Baseline | NAD/DNA pmol/ng 7 Days | Change | % Change |
|---|---|---|---|---|
| Mean | 0.091 | 0.126 | 0.035 | 37 |
| p= | | | 0.005 | |

These results show clearly that the nicotinic acid alkyl esters of the invention increase the amount of NAD in hair follicles. Expressed another way, the energy content of the follicles increased, and the increases, as can be seen, are quite dramatic.

The foregoing disclosure sets forth various features of the invention, which relates to compositions useful in treating hair growth disorders, such as pattern baldness, and the use of these compositions. The compositions comprise a first nicotinic acid alkyl ester, wherein the alkyl chain of the ester, which may be branched or straight chain, contains from 11 to 22 $CH_2$ groups. Especially preferred is the nicotinic acid alkyl ester where the alkyl group contains 14 $CH_2$ groups, i.e., myristyl nicotinate.

The second nicotinic acid alkyl ester is one where the alkyl group, which may also be branched or straight chained, contains from 1 to 10 $CH_2$ groups, preferably 6 to 10 $CH_2$ groups. Especially preferred is the straight chain nicotinic acid alkyl ester octyl nicotinate.

The two nicotinic acid alkyl esters are combined in a formulation, optionally with a carrier, which may be water, a soap, a detergent, or any other standard carrier useful for application to the scalp.

The formulations of the invention may be in any form that is suitable for administering materials to the scalp. Exemplary, but by no means exclusive examples of such forms are topical solutions shampoos, rinses, aerosols, emulsions, crèmes, sprays, lotions, gels, and so forth.

The compositions are used by applying them to the scalp, such as by washing, massaging, and so forth. It is preferred that the formulations be applied at least once a day, preferably at a dose of from about 0.01% to about 10%, w/v for each of the components, more preferably from about 0.1% to about 5% w/v for each component per day. Different dosing regiments may also be used.

A further feature of the invention is a method for treating a hair loss disorder via administering an amount of a nicotinic acid alkyl ester with a straight chain alkyl group consisting of from about 6 to about 22, and preferably from about 8 to about 16 carbon atoms, in an amount sufficient to alleviate, reduce, or otherwise treat hair loss. As was shown, supra, these nicotinic acid alkyl esters cause an increase in intrafollicular $NAD^+$ content, as manifested in an increased $NAD^+/DNA$ ratio, in the hair follicles. Thus, in turn, results in an increase in intrafollicular energy content, which may be the reason for the alleviation of the hair loss.

One or more nicotinic acid alkyl esters may be so used, with the C8 and C14 alkyl chains being especially preferred.

Also a part of the invention is a method for increasing thickness or fullness of pre-existing hair, via the use of the compositions of the invention. It has been observed, as these data show, that the use of these formulations, in addition to alleviating hair loss, results in an increase in hair fullness and/or thickness.

Other aspects of the invention will be clear to the skilled artisan, and need not be reiterated here.

The terms and expression which have been employed are used as terms of description and not of limitation, and there is no intention in the use of such terms and expression of excluding any equivalents of the features shown and described or portions thereof, it being recognized that various modifications are possible with the scope of the invention.

The invention claimed is:

1. A composition for treating a hair loss disorder consisting of:
   (i) a first nicotinic acid alkyl ester, wherein the alkyl moiety of said nicotinic acid alkyl ester is 11 to 22 carbon atoms,
   (ii) a second nicotinic acid alkyl ester, wherein the alkyl moiety of said nicotinic acid alkyl ester is 6 to 10 carbon atoms, and
   (iii) a pharmaceutically acceptable carrier.

2. The composition of claim 1, in the form of a topical solution shampoo, rinse, aerosol, emulsion, lotion, crème, or gel.

3. The composition of claim 1, wherein the second nicotinic acid alkyl ester is octyl nicotinate.

4. The composition of claim 1, wherein the first nicotinic acid alkyl ester is myristyl nicotinate.

* * * * *